United States Patent
Ralston et al.

(10) Patent No.: US 7,365,173 B2
(45) Date of Patent: Apr. 29, 2008

(54) METHOD FOR THE PRODUCTION OF PURE VIRALLY INACTIVATED BUTYRYLCHOLINESTERASE

(75) Inventors: Annemarie H. Ralston, Bethesda, MD (US); Billy L. Kolen, Springdale, MD (US); David John Hammond, Laytonsvile, MD (US)

(73) Assignee: American National Red Cross, Washington, DC (US)

( * ) Notice: Subject to any disclaimer, the term of this patent is extended or adjusted under 35 U.S.C. 154(b) by 1180 days.

(21) Appl. No.: 10/061,233

(22) Filed: Feb. 4, 2002

(65) Prior Publication Data

US 2003/0148488 A1  Aug. 7, 2003

(51) Int. Cl.
C07K 1/14 (2006.01)
C07K 1/18 (2006.01)
C07K 1/22 (2006.01)

(52) U.S. Cl. ............ 530/412; 530/416; 530/422

(58) Field of Classification Search ............ None
See application file for complete search history.

(56) References Cited

U.S. PATENT DOCUMENTS

| | | | |
|---|---|---|---|
| 5,272,080 A * | 12/1993 | Lynch ............ | 435/197 |
| 5,981,254 A * | 11/1999 | Bui-Khac ......... | 435/214 |
| 6,093,804 A * | 7/2000 | Ralston et al. ..... | 530/416 |
| 6,239,261 B1 * | 5/2001 | Heimburger et al. ... | 530/412 |
| 6,251,860 B1 * | 6/2001 | Parkkinen et al. ... | 514/8 |
| 6,326,473 B1 * | 12/2001 | Parkkinen et al. ... | 530/394 |
| 6,924,267 B2 * | 8/2005 | Daemen et al. ..... | 514/8 |
| 7,049,121 B2 * | 5/2006 | Watkins et al. ..... | 435/196 |
| 7,217,507 B2 * | 5/2007 | Hammond et al. ... | 435/5 |

OTHER PUBLICATIONS

Masson. P., et al., 1980, "Purification de la butyrylcholinesterase du plasma humain", Comptes Rendues de l'Acadamies des Sciences, Paris, Serie D, vol. 290, pp. 857-860.*

Masson, P., et al., 1984, "Etude electrophoretique de la butyrylcholinesterase agee apres inhibition par le soman", Biochimie, vol. 66, pp. 235-249.*

Molinari, R., et al., 1990, "Simultaneous ultrafiltration and affinity-sorptive separation of proteins in a hollow fiber membrane module", Biotechnology and Bioengineering, vol. 36, pp. 572-580.*

Treskatis, S., et al., 1992, "Butyrylcholinesterase from chicken brain is smaller than that from serum: Its purification, glycosylation and membrane association", Journal of Neurochemistry, vol. 58, pp. 2236-2247.*

Sine, J.-P., et al., 1996, "Electrostatic interactions of the butyrylcholinesterase dimer of mucosal cells of rat intestine with glycosaminoglycans", International Journal of Cell Biology, vol. 28, No. 5, pp. 581-589.*

Grunwald, J., et al.; 1997, "Large-scale purification and long-term stability of human butyrylcholinesterase, a potential bioscavenger drug", Journal of Biochemical and Biophysical Mthods, vol. 34, pp. 123-135.*

Sarkafati, B., et al., 1999, "Inhibition kinetics of human serum butyrylcholinesterase by Cd2+, Zn2+ and Al3+: Comparison of the effects of metal ions on cholinesterases", Comparative Biochemistry and Physiology, Part C, vol. 122, pp. 181-190.*

\* cited by examiner

*Primary Examiner*—Nashaat T. Nashed
*Assistant Examiner*—William W. Moore
(74) *Attorney, Agent, or Firm*—Buchanan Ingersoll & Rooney PC

(57) ABSTRACT

The present invention provides a method for purifying butyrylcholinesterase from various biological fluids. Biological fluids include, e.g., blood, blood fractions, plasma, and bioreactor broths, and other such mixtures containing butyrylcholinesterase. In one embodiment, the invention provides a method for the production of purified, virally inactivated butyrylcholinesterase by contacting a biological fluid containing butyrylcholinesterase with a cationic exchange chromatography material, with an affinity chromatography material, and treating the fluid with solvent detergent. The resulting purified butyrylcholinesterase can also be subjected to a pasteurization step, and formulated in a sodium chloride/sodium phosphate solution for storage or lyophilization.

25 Claims, No Drawings

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Lys Asp Gln Ile Pro
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Lys Gly Asp Gln Asn
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Lys Asp Ala Val Gln
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)
<223> OTHER INFORMATION: 2-naphthylalanine

<400> SEQUENCE: 4

Gly Phe Val Gly Xaa Ala
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: 2-naphthylalanine

<400> SEQUENCE: 5

Gly Phe His Gly Xaa Ile
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Phe Thr Asn Gly Glu
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Phe Thr Asn Gln Glu
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Thr Asn Tyr His Gln
 1               5

<210> SEQ ID NO 9
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 9

Ala Glu Val Asp Pro Gly
 1               5
```

METHOD FOR THE PRODUCTION OF PURE VIRALLY INACTIVATED BUTYRYLCHOLINESTERASE

FIELD OF THE INVENTION

The present invention provides a method for the isolation and purification of butyrylcholinesterase from complex biological fluids such as plasma. More specifically, the present invention provides a method for purifying and disinfecting butyrylcholinesterase from butyrylcholinesterase-containing biological fluids, e.g., Cohn Fraction IV-4 or IV-1, comprising subjecting such fluids to cationic exchange chromatography, affinity chromatography, a solvent detergent treatment, and pasteurization. As discussed more fully below, the order of those steps can be varied.

BACKGROUND OF THE INVENTION

Butyrylcholinesterase is an enzyme found mainly in plasma. Although the normal physiological role of butyrylcholinesterase is unknown, butyrylcholinesterase has been shown to metabolize acetylcholine, degrade cocaine, and inactivate anaesthetic drugs and muscle relaxants, including succinylcholine, succinylcholine-like compounds and mivacurium (Gorelick et al., *Drug Alcohol Depend.*, 48(3): 159-65, 1997; Stewart et al., *Clin. Pharmacol. Ther.*, 25: 464-8, 1979; Krasowski et al., *Can. J. Anaesth.*, 44:525-34, 1997; Jatlow et al., *Anesth. Anag.*, 58:235-8, 1979). Butyrylcholinesterase has also been shown to act as an antidote to nerve gas and organo-phosphorus compounds (Ashani et al., *Biochem. Pharmacol.*, 41:37-41, 1991; Broomfield et al., *JPET*, 259:633-8, 1991; Doctor et al., New Approaches to Medical Protection Against Chemical Warfare Nerve Agents In Chemical Warfare Agents: Toxicity at Low Levels, pp. 191-214, Lewis Publishers, Inc., 2001; Ashani et al., *Drug Development Research*, 50:298-308, 2000).

Previous methods for isolating butyrylcholinesterase involved either ammonium sulfate precipitations or electrophoresis, which resulted in yields of butyrylcholinesterase of about 10% and purities of 10% or less (Goedde et al., *Humangenetik.*, 1:311-8 1965; Haupt et al., *Blut.*, 14(2):65-75, 1966). Present methods employing chromatography of plasma result in yields of butyrylcholinesterase ranging from 30-40% to 63% (Grunwald et al., *J. Biochem. Biophys. Methods*, 34(2):123-35, 1997; Lockridge et al., *J. Biol. Chem.*, 287:12012-8, 1982). In order to evaluate butyrylcholinesterase for its therapeutic and pharmacological properties, large quantities of purified, virally inactivated butyrylcholinesterase are needed.

Within the art, there remains a need for a method whereby large quantities of virally inactivated butyrylcholinesterase can be isolated from biological fluids such as plasma in a highly purified form. Until now, there have been no commercially viable, easily performed methods to efficiently and economically produce large quantities of purified, virally inactivated butyrylcholinesterase from biological fluids. The methods of the present invention address that need.

SUMMARY OF THE INVENTION

To satisfy the need in the art, we have developed a versatile, commercially viable method for producing purified, virally inactivated butyrylcholinesterase at high yields and purity. Specifically, the present invention provides a novel method for recovering purified, virally inactivated butyrylcholinesterase from a biological fluid such as plasma, Cohn plasma Fraction IV-4 or IV-1, analogous blood fractions, or fluids from bioreactors. The various embodiments of the method comprise subjecting a butyrylcholinesterase-containing fluid to a series of steps including cationic exchange chromatography, affinity chromatography, solvent detergent treatment, and pasteurization. Those steps need not be performed in that order, and the methods can be successfully performed with duplication of one or more of those steps.

DETAILED DESCRIPTION OF THE INVENTION

The inefficient and complex aspects of butyrylcholinesterase purification and viral inactivation can be eliminated using a simple technique employing one or more steps incorporating cation exchange chromatography and affinity chromatography. The method of the invention can be used to produce purified and virally inactivated butyrylcholinesterase from plasma or plasma fractions in yields ranging from about 70% to about 80%. The term pure or purified is used herein to refer to a purity of greater than about 70%. Preferred embodiments afford butyrylcholinesterase in purity of about 80% or greater. The more preferred embodiments afford butyrylcholinesterase in purity of about 90% or greater.

The purity of butyrylcholinesterase is determined by SDS-PAGE analysis and by the specific activity of the final product. Enzymatic activity of the purified butyrylcholinesterase is expressed as mg/mg or units/mg.

Butyrylcholinesterase can be isolated from butyrylcholinesterase-containing sources such as commercially available plasma, plasma fractions such as Cohn Fraction IV-1 or Cohn Fraction IV-4, a mixed plasma fraction of Cohn Fraction IV-1 and IV-4, recombinant sources, and other biological samples. If plasma is used, the plasma can be treated to produce Cohn Fraction IV-4 or IV-1, or plasma fractions of similar composition, as set forth in Cohn et al. (*J. Amer. Chem. Soc.*, 68:459, 1946), or by other methods known in the art.

In accordance with one embodiment of the invention, there is provided a method for producing purified, virally inactivated butyrylcholinesterase from human plasma, in particular Cohn plasma Fraction IV-4. One preferred example of the method comprises subjecting a solution of Cohn plasma Fraction IV-4 to cation exchange chromatography followed by affinity chromatography. A solvent detergent treatment step may be added to inactivate lipid-enveloped viruses; and one or more of the chromatographic steps can be duplicated. The purification portion of the method is versatile, and the order of performing the various steps is not crucial. The purified butyrylcholinesterase is then pasteurized as a general pathogen inactivation step and to inactivate viruses.

The cation exchange chromatography step is performed using any one of a wide variety of cation exchange materials, for example cation exchangers linked to supports such as agarose, dextran, cellulose, polyacrylamide, polystyrene, acrylic polymers, vinyl polymers, and silica. Cation exchangers such as carboxymethyl and sulfopropyl moieties can be linked to, e.g., agarose to produce carboxymethyl-agarose (e.g., CM-SEPHAROSE®) and sulfopropyl-agarose (e.g., SP-SEPHAROSE®), respectively. CM-SEPHAROSE® is a preferred cation exchange material in methods of the present invention.

Cation exchange chromatography can be performed by any of the known methods in the art. Those skilled in the art will appreciate that any conventional format for effectively exploiting cation exchange chromatography materials will be suitable. In a preferred embodiment, column chromatography is used. In such an embodiment, the cation exchange chromatography column is packed with CM-SEPHAROSE® and equilibrated with buffer, preferably about 25 mM sodium acetate, to a pH ranging from about 4.8 to about 5.2 and a conductivity ranging from about 0.85 to about 6.0 mS. Other equilibration buffers encompassed by the method of the invention include but are not limited to sodium citrate and sodium phosphate.

The fall through from the cation ion exchange column contains the butyrylcholinesterase. The resulting biological fluid is adjusted to pH of about 6.0 to about 8.5, more preferably to a pH of about 7.5. The fall through is then concentrated about 5 to about 10 fold by methods known in the art, for example by ultrafiltration or diafiltration, and adjusted to a pH ranging from about 6.0 to about 8.5 and a conductivity ranging from about 6.0 to about 15 mS.

At this stage of the butyrylcholinesterase purification procedure, the fall through concentrate can be solvent-detergent treated before or after an affinity chromatography step. Solvent-detergent treatment involves mixing the fall through or eluate with a solvent such as Tri-n-Butyl Phosphate (TnBP) mixed with a detergent such as the non-ionic detergent Tween-80 or Triton X-100, or combinations thereof, at a concentration ranging from about 0.3% to about 1.0% (w/v) for each solvent-detergent used. Solvent-detergent treatment of the eluate after affinity chromatography is preferable because the volume of eluate being treated is much smaller.

The fall through concentrate from the cation exchange chromatography step is then subjected to affinity chromatography. Again, any conventional method for performing a purification step using affinity chromatography material is acceptable; however, the preferred method is column chromatography. Affinity chromatography materials include, but are not limited to, amino acid resins, peptide ligand resins, antibody resins, carbohydrate resins, avidin/biotin resins, dye resins, glutathione resins, hydrophobic resins, immunochemical resins, lectin resins, nucleic acid resins and nucleotide/coenzyme resins. The term "peptide ligand resins" is used to refer to affinity chromatography matrices to which peptides (i.e., chains of two or more amino acids) are coupled.

In a preferred embodiment of the invention, affinity chromatography is performed using any one of a wide variety of affinity chromatography ligands linked to conventional supports. Conventional supports are matrices such as gels or resins and include, but are not limited to, agarose, dextran, cellulose, polystyrene, acrylic resins, acrylamides, vinyl resins, and cross-linked and/or derivatized variations thereof. One of skill in the art will appreciate that the affinity chromatography support material can be chosen from a variety of commercially available materials, and will be selected from among the various materials such that it has the requisite pore size to accommodate butyrylcholinesterase.

A preferred affinity chromatography material is that in which the support is agarose covalently binding procainamide. Another preferred affinity chromatography material is an agarose support covalently binding a butyrylcholinesterase-binding peptide. Examples of such peptides are presented below.

Commercially available examples of suitable supports include SEPHAROSE® and SEPHADEX® affinity chromatography resins. One of skill in the art will appreciate that many of the supports that are commonly employed in affinity chromatography materials, and which have an appropriate pore size for butyrylcholinesterase will be useful in the present invention. Those supports may be purchased, and preferred ligand can be subsequently coupled to the resin.

As stated above, various materials can be used to perform affinity purification of butyrylcholinesterase from biological fluids. For example, procainamide affinity chromatography material can be employed. Another option is a chromatography material to which is bound an antibody that binds butyrylcholinesterase. Alternatively, other proteins or compounds such as peptide ligands or inhibitors that bind butyrylcholinesterase can be coupled to the resin. Methods for using those additional materials (i.e., antibodies, substrates, compounds, inhibitors, etc.) for affinity chromatography are known within the art.

In one embodiment, the present invention provides a method for producing purified, virally inactivated butyrylcholinesterase comprising: contacting a butyrylcholinesterase-containing biological fluid with a cation exchange chromatography material; solvent-detergent treating the biological fluid; contacting the biological fluid with a butyrylcholinesterase-binding affinity chromatography material; recovering bound butyrylcholinesterase from the affinity chromatography material; and pasteurizing the recovered butyrylcholinesterase. Although it will be appreciated that certain steps will be performed sequentially, it is an advantage of the present invention that several of the foregoing steps can be interchanged in order without sacrificing the effectiveness of the method. Moreover, the purity of the recovered butyrylcholinesterase can be improved by repeating one or more of the steps, particularly the affinity chromatography step.

The method affords the added versatility that when duplicating such steps, different materials can be used. Thus, if one chooses to repeat the affinity chromatography step, different chromatography media can be employed in the two different steps.

Butyrylcholinesterase can be affinity purified from butyrylcholinesterase containing sources using peptide ligands that bind butyrylcholinesterase. In such an embodiment, peptide ligands that bind butyrylcholinesterase are first identified. This can be done by screening combinatorial peptide libraries using labeled butyrylcholinesterase. Butyrylcholinesterase can be labeled using any of the conventional methods in the art, such as radiolabeling. Peptide ligands that are positive for binding butyrylcholinesterase can be detected by using known methods in the art. For example, a conventional enzyme activity assay using butyrylcholine and DTNB (5,5-Dithiobis-2-Nitrobenzoic Acid) can be used. The peptide ligands found to bind butyrylcholinesterase can then be sequenced, and reproduced for isolating and purifying butyrylcholinesterase.

The positive peptide ligands can then be used in such an isolation and purification process in otherwise conventional affinity chromatography methods. In one embodiment, the ligands identified as having the required affinity for butyrylcholinesterase are immobilized on an affinity chromatography support or matrix material. Any common affinity chromatography support or matrix material with the requisite pore size will likely be suitable.

In a preferred embodiment, the ligand(s) are covalently attached to an affinity chromatography matrix to create a matrix-ligand composite. A biological fluid containing butyrylcholinesterase is contacted with the matrix-ligand composite, and butyrylcholinesterase is concentrated on the composite. Extraneous matter and undesired components from the biological fluid are washed away; and the butyrylcholinesterase is subsequently eluted from the composite with appropriate buffers and solutions, and the butyrylcholinesterase is recovered.

The term "biological fluid" is used herein to refer to an aqueous fluid or mixture containing various biological constituents and contaminants in combination with butyrylcholinesterase. In short, a biological fluid, as used herein, is an aqueous mixture of impure butyrylcholinesterase. The butyrylcholinesterase in the biological fluid is either natural or produced from recombinant sources. Examples of biological fluids include blood; blood fractions, plasma, plasma fractions, extracts, and isolates; cell or tissue homogenates, extracts, or isolates; and bioreactor broths or other reaction mixtures suitable for making and/or recovering butyrylcholinesterase. Preferred biological fluids for recovering natural butyrylcholinesterase are Cohn Fractions IV-4, Cohn Fraction IV-1, Precipitate IV (hereinafter "PPT. IV"; also referred to in the art as Precipitate B or PPT. B) from the Kistler-Nitschmann fractionation, and combinations thereof. For a description of PPT. IV see, Kistler P. and Nitschmann H., *Vox. Sanguinis*, 7, 414 (1960).

As discussed below, the various biological fluids, such as plasma fractions, can be reconstituted in water or other appropriate aqueous solvents to achieve the desired density, product concentration, and the like. Selection of aqueous solvent and the amount used for reconstitution will vary depending upon the biological fluid employed, and can be routinely determined by one of ordinary skill in the art.

We have identified the following peptides as preferred peptide affinity ligands for the concentration, separation, and purification of butyryicholinesterase: AKDQIP (SEQ ID NO: 1) (alanine, lysine, aspartic acid, glutamine, isoleucine, proline), AKGDQN (SEQ ID NO: 2) (alanine, lysine, glycine, aspartic acid, glutamine, asparagine), WKDAVQ (SEQ ID NO: 3) (tryptophan, lysine, aspartic acid, alanine, valine, glutamine), GFVGXA (SEQ ID NO: 4) (glycine, phenylalanine, valine, glycine, X, alanine, wherein X is 2-naphthylalanine), GFHGXI (SEQ ID NO: 5) (glycine, phenylaianine, histidine, glycine, X, isoleucine, wherein X is 2-naphthyialanine), AFTNGE (SEQ ID NO: 6) (alanine, phenylalanine, threonine, asparagine, glycine, glutamic acid), AFTNQE (SEQ ID NO: 7) (alanine, phenylalanine, threonine, asparagine, glutamine, glutamic acid), GTNYHQ (SEQ ID NO: 8) (glycine, threonine, asparagine, tyrosine, histidine, glutamine), AEVDPG (SEQ ID NO: 9) (alanine, glutamic acid, valine, aspartic acid, proline, glycine).

In still another embodiment of the present invention, butyrylcholinesterase can be concentrated from a biological fluid in a simple separation of one or more steps. That is, the peptide ligands identified above can be used in a highly versatile and effective one-step method for concentrating and isolating butyrylcholinesterase from biological fluids. Thus, the present invention provides a method for concentrating butyrylcholinesterase comprising contacting a butyrylcholinesterase-containing biological fluid with a peptide ligand affinity chromatography material wherein the peptide ligand is selected from the group consisting of: a) alanine, lysine, aspartic acid, glutamine, isoleucine, and proline; b) alanine, lysine, glycine, aspartic acid, glutamine, and asparagine; c) tryptophan, lysine, aspartic acid, alanine, valine, and glutamine; d) glycine, phenylalanine, valine, glycine, 2-naphthylalanine, and alanine; e) glycine, phenylalanine, histidine, glycine, 2-naphthylalanine, and isoleucine; f) alanine, phenylalanine, threonine, asparagine, glycine, and glutamic acid; g) alanine, phenylalanine, threonine, asparagine, glutamine, and glutamic acid; h) glycine, threonine, asparagine, tyrosine, histidine, glutamine; and i) alanine, glutamic acid, valine, aspartic acid, proline, glycine; and recovering butyrylcholinesterase bound to said peptide ligand chromatography material. The contacting step can be a standard column chromatography method; and the recovery can be performed by eluting the butyrylcholinesterase from the column using known buffers, salt solutions, and solvents.

The simple one-step separation method can be combined with one or more purification and/or disinfection steps. Thus, the peptide ligand affinity separation step can be coupled with a cation exchange step, a solvent detergent treatment step, and/or a pasteurization step.

Further, one or more of the purification steps (i.e., affinity or cation exchange) can be duplicated in a variation of the method. In duplicating one or more of those steps, different media can be employed. For example, in duplicating the affinity separation step, it is possible to use a different peptide ligand or a different class of ligand (e.g., procainamide).

Butyrylcholinesterase can be affinity purified using a variety of affinity chromatography media. In another preferred embodiment, procainamide affinity reagent (p-amino-N-(2-diethylaminoethyl) benzamide) is covalently coupled to 6-aminohexanoic acid agarose using EDC (1-ethyl-3-(3-dimethylaminopropyl) carbodiimide) as a coupling reagent. The affinity chromatography column with procainamide affinity reagent is equilibrated with buffer, preferably 20 mM sodium phosphate and 0.1 M sodium chloride, to a pH ranging from about 6.0 to about 8.5 and a conductivity ranging from about 8 to about 15 mS. Other equilibration buffers encompassed by the method of the invention include but are not limited to Tris and glycine buffers.

As stated above, the eluate from the affinity chromatography column can be solvent-detergent treated. If solvent-detergent treatment is performed at this stage of butyrylcholinesterase isolation, then this solvent-detergent treated eluate is subjected to a second round of affinity chromatography, and the butyrylcholinesterase is eluted from the column with sodium chloride ranging from about 0.3 to about 0.5 M. Solvent-detergent treatment is performed as described above.

The methods of the present invention can be used to inactivate lipid enveloped or non-lipid enveloped viruses. Therefore, the purified butyrylcholinesterase is pasteurized for a time period ranging from about 8 to about 72 hours, preferably from about 8 to about 24 hours, without substantial loss of butyrylcholinesterase activity.

The present methods afford viral inactivation with retention of at least about 80% butyrylcholinesterase activity even after pasteurization for about 72 hours. In one embodiment, pasteurization is performed at about +60° C. for about 8 to about 12 hours in solutions of L-lysine (about 0.1 to about 1.0 M) and sodium citrate (about 0.5 to about 1.0 M); sucrose (about 0.3 to about 0.6 M) and sodium citrate (about 0.6 to about 1.0 M); or sucrose (about 0.6 to about 1.0 M) and glycine (about 0.3 to about 0.5 M). Preferably, pasteurization is performed in a solution of sucrose (about 0.3 to about 0.6 M) and sodium citrate (about 0.6 to about 1.0 M).

Esterolytic activity of butyrylcholinesterase was determined in a standard esterolytic assay with the substrate butyrylthiocholine. Retention of esterolytic activity of butyrylcholinesterase for about 24 hours at about +60° C. was achieved in formulations of about 0.3 to about 0.6M sucrose in varying combinations with about 0.6 to about 1.0

M sodium citrate as well as in a formulation of about 0.1 M lysine and about 1.0 M sodium citrate, as preferred pasteurization formulations.

The following Examples are provided to further illustrate a few embodiments of the present invention. The Examples are presented for illustration only, and do not reflect or suggest any limitation on the scope of the invention.

EXAMPLE I

Purification and Viral Inactivation of Butyrylcholinesterase

Materials: Cohn Fraction IV-4 paste obtained by the Cohn cold ethanol fractionation process of pooled human plasma was used in this example. The cation exchange materials used (CM-SEPHAROSE®, FAST FLOW® OR SP-SEPHAROSE®, FAST FLOW®) are commercially available resins.

The affinity resin was prepared by coupling procainamide covalently to ECH-SEPHAROSE 4B® (Pharmacia) using EDC as a coupling reagent. Procainamide was added in 5-fold molar excess per gram of swollen gel relative to the resin ligands. EDC was then added to a final concentration of about 0.1 M. The coupling procedure was performed in distilled water, adjusted to a pH ranging from about 4.5 to about 5.5 with HCl. The procainamide/EDC mixture was rotated gently for about 24 hours at room temperature, and the resin was subsequently washed with several cycles of high and low pH solutions (0.1 M acetate buffer, 0.5 M NaCl pH 4.0; 0.1 M Tris-HCl buffer; 0.5 M NaCl, pH 8.0), followed by washes with distilled water. The resulting resin was stored in about 20% ethanol.

In this example, the method of the invention was performed as follows: 1.0 kg of Cohn IV-4 was suspended in about 8.0 L of distilled water (optionally containing 1.0 mM EDTA) to form a mixture and stirred for about 2 hours or overnight at about 4° C. Particulate matter such as insoluble proteins and Celite, an additive added to collect Cohn Fraction IV-4, was removed by centrifugation at about 4000 g and clarified through 5 µm, 1.0 µm, 0.5 µm and 0.2 µm filters. After adjusting the pH to a range from about 4.9 to about 5.1 with acetic acid and the conductivity to between about 0.85 to about 1.3 mS with distilled water, the mixture was loaded on a cation exchange chromatography column packed with approximately 0.35 L-0.5 L of CM-SEPHAROSE®, which had been equilibrated with about 25 mM sodium acetate (pH 4.9; conductivity 1.8 mS; temperature 22° C.), at a linear velocity of about 60 cm/H and a residence time ranging from about 10 to about 12 minutes (if SP-SEPHAROSE® resin is used, the pH is about 5.2 and the conductivity is about 6.0 mS). The column was washed with about 0.5 L of 25 mM sodium acetate buffer (pH 4.9), and the wash was added to the fall through to collect the butyrylcholinesterase quantitatively. The specific advantage of this chromatographic step was that the butyrylcholinesterase remained in the fall through while greater than 90% of the contaminating proteins were bound to the cation exchange material.

The fall through, which contains the butyrylcholinesterase, was adjusted to a pH of about 7.5 with about 1.0 M NaOH and then concentrated 5 to 10 fold by ultrafiltration using a membrane with a molecular weight cutoff of about 100,000. After concentrating the fall through, the conductivity was adjusted to about 9.5 mS with about 4.0 M NaCl.

The concentrate from above was then loaded onto an affinity chromatography column packed with approximately 0.05-0.075 L of procainamide (PAM) affinity resin, which had been equilibrated with about 20 mM sodium phosphate and about 0.1 M sodium chloride (pH 7.5; conductivity 10.5 mS), at a linear velocity of about 50 cm/H. The column was washed step-wise with about 0.1, 0.15, 0.175 and 0.2 M NaCl in about 20 M sodium phosphate (pH 7.5) and then eluted with about 0.4 L of 0.5 M NaCl and 20 mM sodium phosphate (pH 7.5).

At this stage of the butyrylcholinesterase purification procedure, the eluted butyrylcholinesterase was treated with solvent-detergent. Solvent-detergent treatment involved mixing the PAM affinity eluate fall through with about 1% (v/v) Tween-80 and about 0.3% (v/v) TnBP.

The eluate was then subjected to a second round of PAM affinity chromatography and washed and eluted as described above. The yield and purity of the isolated butyrylcholinesterase was calculated to be about 80% and about 80-90%, respectively.

To inactivate both lipid and non-lipid enveloped viruses, such as porcine parvo virus (PPV) (which is used as a model virus for human B19 parvovirus), in the purified butyrylcholinesterase, the eluate from the second PAM affinity chromatography step was pasteurized at about +60° C. for about 24 hours in a solution of sucrose and sodium citrate or lysine and sodium citrate or glycine and sucrose.

We found that combinations of sucrose (about 0.3 to about 0.6 M) with varying concentrations of sodium citrate (about 0.6 to about 1.0 M) or the combination of lysine (about 0.1 to about 0.5 M) with sodium citrate (about 1.0 M) allowed pasteurization of butyrylcholinesterase in liquid form at about +60° C. with greater than 95% butyrylcholinesterase activity remaining and greater than a $10^4$ reduction in PPV. The final butyrylcholinesterase product can be subjected to diafiltration or ultrafiltration before formulation. Butyrylcholinesterase can be formulated in liquid form in about 0.1 to about 0.15 M NaCl and about 0.02 M sodium phosphate buffer (pH about 6.5 to about 7.5) and stored in liquid for or it can be lyophilized.

The process may readily be scaled up. For example, when processing about 150 kg of biological fluid, such as Cohn Fraction IV-1 or IV-4, we recommend using approximately 55-70 L of cation exchange resin and approximately 7.5-10 L of PAM resin.

EXAMPLE II

Affinity Purification of butyrylcholinesterase Using Peptide Ligands

Identification of positive peptides: Solid phase combinatorial peptide libraries were synthesized on polymethacrylate beads (Buettner et al, *Int. J. Pep Prot. Res.,* 47, 70-83 (1996)) and screened for the binding of butyrylcholinesterase using the radiolabeled technique of Jentoft et al. (*Methods in Enzymology,* 91:570-79 (1983)) to radiolabel butyrylcholinesterase. To detect positive ligands that bind butyrylcholinesterase, the screening method of Mondorf et al. (*J. Peptide Res.,* 52(6):526-36 (1998)) combined with an activity assay using the substrate butyrylthiocholine and DTNB (5,5-Dithiobis-2-Nitrobenzoic Acid) were used. This stained the beads that bound active butyrylcholinesterase yellow.

We have identified the following ligands as useful and effective for the affinity purification of butyrlcholinesterase: AKOQIP (SEQ ID NO: 1) (alanine, lysine, aspartic acid, glutamine, isoleucine, proline), AKGDQN (SEQ ID NO: 2) (alanine, lysine, glycine, aspartic acid, glutamine, asparagine), WKDAVQ (SEQ ID NO: 3) (tryptophan, lysine, aspartic acid, alanine, valine, glutamine), GFVGXA (SEQ ID NO: 4) (glycine, phenylalanine, valine, glycine, X, alanine, wherein X is 2-naphthylalanine), GFHGXI (SEQ ID NO: 5) (glycine, phenylalanine, histidine, glycine, X, isoleucine, wherein X is 2-naphthylalanine), AFTNGE (SEQ ID NO: 6) (alanine, phenylalanine, threonine, asparagine, glycine, glutamic acid), AFTNQE (SEQ ID NO: 7) (alanine, phenylalanine, threonine, asparagine, glutamine, glutamic acid), GTNYHQ (SEQ ID NO: 8) (glycine, threonine, asparagine, tyrosine, histidine, glutamine), AEVDPG (SEQ ID NO: 9) (alanine, glutamic acid, valine, aspartic acid, proline, glycine).

Any of those ligands, or other butyrylcholinesterase-binding peptides, can be immobilized on an affinity matrix material, and used in affinity separations methods to concentrate, isolate, and recover butyrylcholinesterase from, e.g., plasma, Cohn Fract IV-1, Cohn Fraction IV-4, and other biological fluids containing butyrylcholinesterase in combination with other proteins and extraneous biological matter. It will be appreciated by those skilled in the art that, in view of the present disclosure, one of skill in the art will be able to identify additional such peptides having the desired level of affinity, and reversible binding properties with butyrylcholinesterase. Accordingly, the foregoing peptide ligands are illustrative only and the recitation of those ligands herein should not be construed as a limitation on the scope of the invention or of the potential ligands useful in the present invention.

Numerous modifications and variations of the methods of the present invention are possible in light of the foregoing disclosure. Therefore, one of skill in the art will understand that the invention can be exploited otherwise than as specifically described herein.

All references cited herein are incorporated herein by reference in their entirety.

The invention claimed is:

1. A method for producing a composition comprising a purified butyrylcholinesterase free of active virus wherein the first step is contacting a butyrylcholinesterase-containing biological fluid with an ion exchange chromatography material consisting of a cation exchange chromatography material and allowing the butyrylcholinesterase to flow through the cation exchange chromatography material wherein said first step is followed by the subsequent steps comprising steps a through d and wherein step a may optionally follow steps b and c:
   a. solvent-detergent treating the butyrylcholinesterase-containing fall-through;
   b. contacting the butyrylcholinesterase-containing fall-through with a butyrylcholinesterase-binding affinity chromatography material;
   c. recovering bound butyrylcholinesterase from the affinity chromatography material; and
   d. pasteurized the recovered butyrylcholinesterase thereby obtaining a composition comprising a purified butyrylcholinesterase free of active virus.

2. The method of claim 1, wherein either or both of the first step and a step b are repeated.

3. The method of claim 1, wherein the butyrylcholinesterase containing biological fluid comprises a plasma fraction selected from the group consisting of Cohn Fraction IV-4, Cohn Fraction IV-1, Precipatate IV from a Kistler-Nitschmann fractionation, and combinations thereof.

4. The method of claim 1, wherein the butyrylcholinesterase-containing biological fluid comprises recombinantly produced butyrylcholinesterase.

5. The method of claim 1, wherein said cation exchange material is a cation exchanger linked to a support selected from the group consisting of agarose, dextran, cellulose, polyacrylamide, polystyrene, acrylic polymers, vinyl polymers, and silica.

6. The method of claim 1, wherein said cation exchange material comprises a carboxymethyl moiety or a sulfopropyl moiety.

7. The method of claim 1, wherein said affinity chromatography material is selected from the group consisting of peptide ligand resins, carbohydrate resins, dye resins, immunochemical resins, lectin resins, nucleic acid resins, and nucleotide/coenzyme resins.

8. The method of claim 1, wherein said affinity chromatography material comprises a support selected from the group consisting of agarose, dextran, cellulose, polystyrene, an acrylic resin, an acrylamide resin, and a vinyl resin, and covalently attached to said support is procainamide.

9. The method of claim 1, wherein said affinity chromatography material comprises an agarose support to which is covalently bound procainamide or a butyrylcholinesterase-binding peptide ligand.

10. The method of claim 9, wherein the butyrylcholinesterase-binding peptide ligand is selected from the group consisting of:
   a. SEQ ID NO:1;
   b. SEQ ID NO:2;
   c. SEQ ID NO:3;
   d. SEQ ID NO:4;
   e. SEQ ID NO:5;
   f. SEQ ID NO:6;
   g. SEQ ID NO:7;
   h. SEQ ID NO:8; and
   i. SEQ ID NO9.

11. The method of claim 1, wherein said pasteurization of butyrylcholinesterase is performed at about +60° C. for a time period ranging from about 8 to about 72 hours.

12. The method of claim 1, wherein said pasteurization of butyrylcholinesterase is performed at about +60° C. in a L-lysine/sodium citrate solution or a sucrose solution for a time period of at least about 8 hours.

13. The method of claim 12, wherein said sucrose solution is Sucrose/Sodium Citrate or Sucrose/Glycine.

14. The method of claim 1, wherein said pasteurized butyrylcholinesterase is formulated in about 0.1 to about 0.15 M NaCl and about 0.02 M sodium phosphate.

15. A method for producing a composition comprising a purified, butyrylcholinesterase free of active virus wherein the first step is contacting a butyrylcholinesterase-containing biological fluid with an ion exchange chromatography material consisting of a cation exchange chromatography material and allowing the butyrylcholinesterase to flow through the cation exchange chromatography material wherein said first step is followed by the subsequent steps:
   a. contacting the butyrylcholinesterase-containing fall-through with a butyrylcholinesterase-binding affinity chromatography material;
   b. recovering butyrylcholinesterase from the affinity chromatography material;
   c. solvent-detergent treating the butyrylcholinesterase recovered from the affinity chromatography material;
   d. contacting the solvent-detergent treated product with a butyrylcholinesterase-binding affinity chromatography material;
   e. recovering butyrylcholinesterase from the affinity chromatography material; and
   f. pasteurizing the recovered butyrylcholinesterase thereby obtaining a composition comprising a purified butyrylcholinesterase free of active virus.

16. The method of claim 15, wherein the butyrylcholinesterase-containing biological fluid comprises a plasma fraction selected from the group consisting of Cohn Fraction IV-4, Cohn Fraction IV-1, PrecipatateIV from a Kistler-Nitschmann fractionation, and combinations thereof.

17. The method of claim 15, wherein the butyrylcholinesterase-containing biological fluid comprises recombinantly produced butyrylcholinesterase.

18. The method of claim 15, wherein said cation exchange chromatography material comprises a carboxymethyl moiety or a sulfopropyl moiety.

19. The method of claim 15, wherein said affinity chromatography material is selected from the group consisting of peptide ligand resins, carbohydrate resins, dye resins, immunochemical resins, lectin resins, nucleic acid resins, and nucleotide/coenzyme resins.

20. The method of claim 15, wherein said affinity chromatography material comprises an agarose support to which is covalently bound procainamide or a butyrylcholinesterase-binding peptide ligand.

21. The method of claim 20, wherein the butyrylcholinesterase-binding peptide ligand is selected from the group consisting of:
    a. SEQ ID NO:1;
    b. SEQ ID NO:2;
    c. SEQ ID NO:3;
    d. SEQ ID NO:4;
    e. SEQ ID NO:5;
    f. SEQ ID NO:6;
    g. SEQ ID NO:7;
    h. SEQ ID NO:8; and
    i. SEQ ID NO:9.

22. The method of claim 15, wherein said pasteurization of butyrylcholinesterase is performed at about +60° C. for a time period ranging from about 8 to about 72 hours.

23. The method of claim 15, wherein said pasteurization of butyrylcholinesterase is performed at about +60° C. in a L-lysine/sodium citrate solution or a sucrose solution for at least about 8 hours.

24. The method of claim 23, wherein said sucrose solution is Sucrose/Sodium Citrate or Sucrose/Glycine.

25. The method of claim 15, wherein said pasteurized butyrylcholinesterase is formulated in about 0.1 to about 0.15 M NaCl and about 0.02 M sodium phosphate.

* * * * *